United States Patent [19]

Cohen et al.

[11] Patent Number: 5,685,992
[45] Date of Patent: Nov. 11, 1997

[54] PROCESS FOR REGULATING AT LEAST ONE FLUID FLOW CIRCULATING IN A SIMULATED MOVING BED CHROMATOGRAPHIC SEPARATION LOOP

[75] Inventors: Choua Cohen, Lyons; Robert Jacob, Chaponost; Gérard Bureau du Colombier, Oullins; Gérard Hotier, Rueil Malmaison, all of France

[73] Assignee: Institut Francais du Petrole, Rueil-Malmaison, France

[21] Appl. No.: 773,782

[22] Filed: Dec. 26, 1996

[30] Foreign Application Priority Data

Dec. 27, 1995 [FR] France .................. 95 15526

[51] Int. Cl.⁶ .................................................. B01D 15/08
[52] U.S. Cl. .......................... 210/659; 210/198.2
[58] Field of Search ........................ 210/635, 656, 210/659, 662, 198.2; 585/821, 825, 828

[56] References Cited

U.S. PATENT DOCUMENTS

| | | | |
|---|---|---|---|
| 2,985,589 | 5/1961 | Broughton | 210/659 |
| 3,268,605 | 8/1966 | Boyd, Jr. | 260/666 |
| 4,447,329 | 5/1984 | Broughton | 210/673 |
| 4,498,991 | 2/1985 | Oroskar | 210/659 |
| 5,093,004 | 3/1992 | Hotier | 210/659 |
| 5,102,553 | 4/1992 | Kearney | 210/659 |
| 5,114,590 | 5/1992 | Hotier | 210/659 |
| 5,422,007 | 6/1995 | Nicoud | 210/659 |
| 5,470,482 | 11/1995 | Holt | 210/662 |

FOREIGN PATENT DOCUMENTS

| | | | |
|---|---|---|---|
| 2 550 462 | 2/1985 | France | 210/198.2 |
| 91/08815 | 6/1991 | WIPO | 210/198.2 |
| 92/16274 | 10/1992 | WIPO | 210/198.2 |

*Primary Examiner*—Ernest G. Therkorn
*Attorney, Agent, or Firm*—Millen, White, Zelano & Branigan, P.C.

[57] ABSTRACT

A process for regulating at least one flow of at least one fluid or effluent circulating in a simulated moving bed comprising columns which form a closed loop containing at least one device such as a recycling pump introducing a pressure anisotropy. Every time an injection or extraction point passes from one part of the pump to the other, a control device which controls a fluid flow regulating means for the fluid under consideration, regulated about a set value, is caused to stop regulation temporarily, and substantially simultaneously the regulating means is placed in a position which allows it to approach the desired value, preferably to reach the desired flow rate and to begin to regulate the flow rate about the desired set value, to keep the flow rates in all the zones in a simulated moving bed constant. The process is especially applicable Application to the separation of para-xylene from a mixture of xylenes.

16 Claims, No Drawings

PROCESS FOR REGULATING AT LEAST ONE FLUID FLOW CIRCULATING IN A SIMULATED MOVING BED CHROMATOGRAPHIC SEPARATION LOOP

BACKGROUND OF THE INVENTION

The invention concerns a process for regulating the flow of at least one effluent in a chromatographic zone containing a fixed phase, for example an adsorbent or a molecular sieve. More particularly, it concerns the regulation of flows in a simulated moving bed adsorption zone, which may be in counter-current or co-current mode.

It is of particular application to the separation of paraxylene from aromatic hydrocarbon feeds containing eight carbon atoms.

The prior art is illustrated in the following patents: U.S. Pat. No. 2,985,589, U.S. Pat. No. 3,761,533, U.S. Pat. No. 4,402,832, U.S. Pat. No. 4,498,991, U.S. Pat. No. 5,284,992, U.S. Pat. No. 5,470,482, U.S. Pat. No. 3,268,605, International patents WO-A-92 16274, WO-A-91 08815 and French patent FR-A-2 550 462, which are hereby incorporated by set.

A simulated moving bed comprises at least three chromatographic zones, advantageously four or five, each of these zones being constituted by at least one column or column section. At least one point between two zones is for injection of a feed to be fractionated and at least one point between two zones is for injection of eluent. Further, the simulated moving bed comprises at least one extract extraction point between the eluent injection point and the feed injection point located downstream in the direction of circulation of the eluent and at least one raffinate extraction point between each mixture injecting point and the eluent injection point located downstream in the direction of circulation of the eluent.

SUMMARY OF THE INVENTION

The ensemble of columns or sections forms at least one closed loop containing at least one recycling pump, between two sections, which is flow rate regulated (between the first and last section, for example).

The injection and extraction points of at least one column or section are generally shifted over time in the same direction (downstream or upstream).

It is vital to respect the flow rates of the effluents circulating from one zone to another, which flow rates must remain substantially constant in a given zone. A slight variation in flow rate even within a single zone can have a great influence on separation.

As an example, we shall consider the case of a simulated moving bed in counter-current mode comprising four zones with a recycling pump, two inlet streams, the eluent and the feed, and two outlet streams, the extract and the raffinate.

Zone 1 is located between the solvent and the extract, zone 2 is located between the extract and the feed, zone 3 is located between the feed and the raffinate and zone 4 is located between the raffinate and the solvent. The flow rates in the different zones are as follows when the pump is in zone 1, for example:

Flow rate in zone 1: flow rate of the pump;
Flow rate in zone 2: flow rate in zone 1–flow rate of extract;
Flow rate in zone 3: flow rate in zone 2+flow rate of feed;
Flow rate in zone 4: flow rate in zone 3–flow rate of raffinate.

Any errors in inlet and outlet streams thus have repercussions on the recycle flow rate and must therefore be precisely controlled.

Every time that one of the inlet or outlet streams of the loop passes from one part of the recycling pump to the other, for example from a position immediately anterior to a position immediately posterior to the recycling pump when operating in simulated counter-current, two difficulties arise as regards regularity of the flow rams:

The first difficulty concerns the recycling pump, when it changes zone. It is very important that the flow rate is modified almost instantaneously and the new flow rate, that of the new zone in which it finds itself, is precisely regulated in stable fashion without passage from one flow rate to another being asymptotic (damped regulation) or fluctuating about the new value (if regulation has rapid action).

This first technical problem is related to the change in zones. It is very important that the flow rate passes instantaneously from a first value to a further desired value. It has been shown, for example, that a variation in the recycling flow rate of 0.6% can produce a variation of 4.2% in purity. It appears that a flow rate regulator, which regulates the flow in stable fashion, and to which a new setting is supplied, takes a certain amount of time to regulate to the new value. Since passage from one flow rate to another must be rapid, the gain of the regulator must be high. In this case, regulation is not very stable. We thus have a choice between rapid but fluctuating regulation or fine and stable regulation which has inertia. These two solutions are not acceptable when regulating a simulated moving bed in which the aim is to obtain high purity.

The second difficulty concerns the flow rate of the stream entering or leaving the unit. The flow rate of this stream must be kept constant with very high precision, while its injection point, or extraction point, passes from a low pressure, the intake pressure of the pump, to a high pressure, the lift pressure of the pump (the pressure difference corresponds to the pressure drop in the ensemble of columns or column sections).

Resolution of these problems is important in order to obtain good separation.

The proposed solution to these problems consists of not allowing the regulator to act alone but, by using a control device, a computer, or any other means which can act on the regulator, to cause the regulator to stop regulating temporarily, and simultaneously to cause it to modify its action, so that the new action, such as a percentage opening of a valve, a current frequency for a motor, a voltage, etc., corresponds to the new conditions to ensure good regulation of the flow rate under consideration, and then, but in fact almost immediately, to restart the action of the regulator:

in the case of the recycling pump, to change the flow rate from one zone to the next;

in the case of an effluent, to maintain a flow rate in the presence of a large variation in pressure conditions.

In this fashion, good flow rates are obtained practically instantaneously and without fluctuations. The operations described last a total of $\frac{1}{100}$ to 10 seconds, generally $\frac{1}{10}$ to 5 seconds, depending on the case.

It should be noted that, in the case of a simulated moving bed in counter-current mode, the problem is substantially the same, with the exception that the changes in the settings for the recycling pump (flow rate regulated) take place every time that one of the inlet or outlet streams passes from a position immediately posterior to a position immediately anterior of the recycling pump.

More generally, the aim of the invention is to maintain the flow rates in each zone as constant as possible by acting on regulation of the recycling pump every time it changes zone, and to remedy perturbations in the flow rates of the extract, raffinate, solvent and feed caused by the pressure change from one part to the other of the recycling pump.

By maintaining constant the extract, raffinate, solvent and feed flow rates whatever the injection or extraction point and by "stepping" passage of the flow rate of one recycling zone to the flow rate in the following zone for the pump, constant flow rates are ensured in the four zones, and a stable concentration profile is maintained for the different constituents without modifying anything else but its displacement in the unit.

Perturbations in the raffinate, extract, solvent and feed flow rates cause a variation in the flow rates in the 4 zones, which renders the unit less stable and reduces performance. In addition, in the case of the extract, surges in the flow rate cause extraction of impurities (initially present in the feed, consisting of extracting ethylbenzene, meta-xylene and ortho-xylene) which reduces the purity. In the case of the raffinate, surges in the flow rate cause extraction of para-xylene, reducing the yield.

More generally, if as is often the case, a recycling pump is used in which the flow rate is controlled and one or more pressure controlled recycling pumps are used, the problem of one or more pressure anisotropies in the counter-current simulated moving bed, for example, is resolved in the same fashion:

Every time the extract E or raffinate R extraction point or feed C or eluent S injection point or internal reflux point R1 passes from a connection to the recycling loop located upstream of an anisotropy to a connection to the recycling loop located immediately downstream of the anisotropy, causing a pressure variation, there may be a perturbation in the flow rates if the action described in the present invention is not taken. Regulation of all the flow rates is refined by using a control device, a computer, or any other means which can act on the regulators to cause the regulator to stop regulating temporarily, and simultaneously to cause it to modify its action, so that the new action caused, such as a percentage opening of a valve, a current frequency for a motor, a voltage, etc., corresponds to the new conditions to ensure good regulation of the flow rate under consideration, and then, but in fact almost immediately, to restart the action of the regulator, thus very rapidly achieving good flow rates without fluctuation.

While the principal cause of an anisotropy of pressure in the simulated moving bed chromatographic unit is the recycling pump(s) or compressor(s), the introduction of other apparatus between two particular columns will produce the same effects: certain measuring or sampling apparatus can be cited, such as flowmeters, spectrometer cells for on-line composition measurement, a by-pass or a sampling loop. Each particular pressure anisotropy, and thus each pressure drop induced by:

introducing a particular apparatus;
passing from one column to the next (with or without a circulating pump) can be compensated for by acting on the regulators as described above each time an injection point or an extraction point passes from the upstream connection to the connection downstream of the anisotropy or the downstream connection to the connection upstream of the anisotropy, depending on whether the operation is in counter-current or co-current mode.

A case of anisotropy which is of particular interest can also result from a one-off pressure drop due to an initial imperfection in one device of the chromatographic unit, or produced during operation at one point in the loop. It may be a partially obstructed conduit, a valve with a higher pressure drop than usual or any other minor problem which does not cause the unit to be stopped, as long as a total pressure drop is permissible for the required flow rate. It can also be a one-off pressure drop in a device such as a sensor which in the absence of particular regulation would perturb one or more flows, and thus all the flows in the zones and can thus affect the purity, yield and stability of the unit. As soon as it is detected, this type of anisotropy can be regulated as described above.

The solution proposed by the invention can be used between two successive beds if a one-off pressure drop problem occurs, which means that production can continue with the same performances and can delay or even avoid stopping the unit.

Further, when one-off pressure drops occur, the overall pressure drop is larger, which in the absence of regulation carried out in accordance with the invention will perturb the extract and/or raffinate flow rates still more and, in general, the flow rates of the effluents during passage from one part to another of the recycling pump.

Excellent results have been obtained using a regulator with low gain adjustments to perfectly stabilise the flow rate and intervene using a control centre which, by means of a control program, modifies the action of the regulator (valve opening, for example) as soon as the zone changes so as to very rapidly produce a flow rate which is close to the desired new value and only thereafter, to cause the regulator to act to maintain the new setting.

More precisely, the invention provides a process for regulating at least one flow rate of at least one fluid or effluent circulating in a simulated moving bed chromatographic adsorption unit containing an adsorbent and comprising at least three chromatographic zones, each of these zones being constituted by at least one column or column section, at least one point between two zones for injection of a feed to be fractionated, at least one point between two zones for injection of eluent, at least one extract extraction point between each eluent injection point and the feed injection point located downstream in the direction of circulation of the eluent and at least one raffinate extraction point between each point for injecting the mixture and the eluent injection point located downstream in the direction of circulation of the eluent, the ensemble of the columns or sections forming at least one closed loop containing at least one device for introducing an anisotropy of properties, the injection and extraction points of at least one column or section being shifted over time in the same direction (downstream or upstream), the process being characterized in that each time that an injection point or an extraction point passes from one part to another of said device, a control device which controls a means for regulating the flow rate under consideration, which regulation is about a set value, is caused to stop temporarily and substantially simultaneously, said regulating means is caused to place itself in a position allowing it to approach the desired flow rate, and preferably to achieve said desired flow rate and to start to regulate said flow rate at the desired set value.

As stated above, the device which can introduce an anisotropy of properties is, in particular, at least one recycling pump which introduces a pressure anisotropy.

In a first implementation of the process, two different flow rates can be used during passage of a fluid or effluent from one zone to the next zone, each of said flow rates being regulated about a set value (a) and (b) and in which passage from a first flow rate (a) to a second flow rate (b) which is different to flow rate (a) is caused by causing a control device controlling the regulating means which is regulating about set value (a) to stop regulating temporarily and to cause the regulating means to place itself in the position allowing it to approach flow rate (b) and start to regulate flow rate (b) about the set value corresponding to flow rate (b).

The term "recycling pump" should be understood to mean the generic term for a circulating means, a pump in the case of a liquid mixture or a pumpable supercritical fluid, and a compressor in the case of a gas mixture under pressure or a less dense supercritical fluid.

In a second implementation of the process, the first and last columns are connected by at least one recycling pump, and a pressure drop ΔP is established between the two columns and in which each time one of the extraction points passes from upstream to downstream of the pump or from downstream to upstream of the pump, the control device controlling the regulating means for the effluent flow rate which is regulated about a set value is caused to stop regulating temporarily and said regulating means is caused to place itself in the position allowing said regulating means to approach said flow rate for the new pressure P+ΔP and to start to regulate said flow rate about the set value.

The flow rate regulating means can be a variable opening valve, a variable speed pump which can operate by varying the frequency or voltage, a variable piston stroke pump or a means which can vary the flow rate by varying the pressure.

The feed which is to be recovered, for example very high purity para-xylene for the synthesis of terephthalic acid for the manufacture of synthetic fibres, can comprise a mixture of aromatic hydrocarbons containing 8 carbon atoms.

It can be constituted by a mixture of aromatic hydrocarbons containing ten carbon atoms from which para-diethylbenzene is to be recovered for use as an eluent in an adsorption zone comprising a zeolite in which a xylene mixture is circulating.

In a variation of the process of the invention, when the injected and extracted fluids are managed by means of an on-off valve per column section and per stream, as the bed are shifted, it is preferable to begin opening the valve of bed P+1 before closing the valve of bed P in order to avoid any interruption in the streams. When one of the injected or extracted streams passes from upstream to downstream of one of the pressure anisotropies or furnishes the connections of each of the streams which are removed and extracted from the last to the first bed, non-return valves are required since for a short period, two valves distributing a given stream are simultaneously open to two locations of the loop where the pressures are very different. During the short period where the two valves are open simultaneously, the regulation vane for the stream is caused to act and the recycling flow rate is changed by causing the recycling flow rate regulating valve to act.

Large perturbations in pressure result both in the closed recycling loop and in the lines in which each of the four streams circulate. A further aim of the invention is to limit pressure surges in the recycling loop. These latter, when too large, weaken and wear the distributors separating each bed and may damage the fixed phase by creating fine particles.

Since the aim of the invention is to limit the deleterious effects of anisotropies in pressure, we have also noticed that desynchronising the passage from upstream to downstream of the pressure anisotropy of each stream and the change in the recycling flow rate can limit pressure surges. In other words, in this variation a fluid or effluent flow is commenced downstream of an anisotropy by opening the downstream valve before stopping the flow upstream by closing the upstream valve, in the case of simulated counter-current, and in the case of simulated co-current, commencing a flow upstream of the anisotropy before stopping the downstream flow, given that the time during which the valves upstream and downstream of the anisotropy are simultaneously open is very brief: generally at most two seconds, and preferably less than one second.

The regulation process of the invention can be carried out in separation units, for example for very high purity para-xylene (more than 99.5%), operating solely in adsorption mode, possibly combined with isomerisation. A fortiori, the process of the invention can be carried out in units combining adsorption, from which a product of lesser purity (for example less than 95%) is recovered, combined with isomerisation and followed by at least one crystallisation step, such as those described in our European patent EP-B-0 531 191, and in our U.S. Pat. No. 5,284,992 and U.S. Pat. No. 5,401,475.

The invention will be better understood from the following examples.

EXAMPLE 1 (prior art)

A counter-current simulated moving bed comprising 24 columns for separating a mixture of xylenes containing 20% of para-xylene was used. The operating conditions were as follows:

Sieve: faujasite exchanged with at least one cation from group IA or group IIA or by a combination of a cation from group IA and from group IIA;

Weight ratio of solvent to feed: 1.6;

Solvent: para-diethylbenzene.

The apparatus comprised conventional regulation of the extract flow (from which para-xylene was extracted), the feed raffinate flow, the solvent flow and the four flows from the recycling pump.

Given that the overall pressure drop in the simulated counter-current separation unit was 14 bars with a single recycling pump, the intake pressure of the pump was 8 bars, for example, and the lift pressure was 22 bars. The extract flow rate measured the flow rate, and then controlled a valve which sent the extract to a receptacle at 2 bars. On passing from position 1 at the pump lift where the pressure was 22 bars to position 24 where the pressure was 8 bars, it gradually opened the extraction valve further and further to ensure the flow rate. In position 24, the valve was 70% open, for example, for an upstream-downstream pressure difference of 6 bars. In position 1, where the pressure was 22 bars at the beginning of the period, the valve was always 70% open, and the upstream-downstream pressure difference of the valve was then 20 bars instead of 6 bars, and the flow rate was, to a first approximation, proportional to the square root of the upstream-downstream pressure difference. From changing to the downstream position of the recycling pump, the pressure difference passed from 20 bars to 6 bars (the ratio of 20 to 6 is 3.33), the desired extract flow rate A passed from A to 1.82 A (1.82 being the square root of 3.33). The conventional regulator gradually closed the extraction valve and the operation lasted about 30 seconds during which the valve stabilised at about 52% open, a value for which, at a pressure difference of 20 bars, the flow rate was once again A. During the whole of the time it took to recover the flow rate, the flow rate was on average multiplied by 1.4 for a period, and as a consequence, the purity was lower during that period and the unit was out of balance and required a number of periods to recover the maximum para-xylene purity. The problem was identical for regulation of the valve which ensured the raffinate flow rate by regulating the unit pressure.

Each time it passed to a new zone, the recycling pump received the new flow rate setting and only achieved this new flow rate value after about 30 seconds.

Under these conditions, separation produced an overall result in which the purity of the para-xylene in the extract was 99% and the yield was 95%.

EXAMPLE 2 in accordance with the invention)

The apparatus of the comparative example was used, but regulation was controlled in accordance with the invention was applied to control the extract flow and raffinate flow, and the four flow rates of the recycling pump.

Given that the overall pressure drop in the simulated counter-current separation unit was 14 bars with a single recycling pump, the intake pressure of the pump was 8 bars, for example, and the lift pressure was 22 bars. The extract flow rate regulator measured the flow rate, and then controlled a valve which sent the extract to a receptacle at 2 bars. On passing from position 1 at the pump lift where the pressure was 22 bars to position 24 where the pressure was 8 bars, it gradually opened the extraction valve further and further to ensure the flow rate. In position 24, the valve was 70% open, for example, for an upstream-downstream pressure difference of 6 bars. In position 1, where the pressure was 22 bars at the beginning of the period, in accordance with the invention, the valve was closed to 52% and this was maintained for ½ a second before allowing the regulation to act. The upstream-downstream pressure difference of the valve was then 20 bars instead of 6 bars in the anterior position and the extract flow rate remained stable at the desired value E.

The problem was identical for the regulation of valves ensuring flow rates R for the raffinate, F for the feed, S for the solvent which were maintained at the opening corresponding to 20 bars pressure difference for 1.5 seconds.

The recycling pump, where flow rate regulation acted on the speed of the motor by varying the current frequency, received the new flow rate setting at each passage to a new zone and at the same time received a new motor frequency corresponding to the desired new flow rate, which value was maintained for 2 seconds before allowing the regulation to act.

Under these conditions, separation produced an overall result in which the purity of the para-xylene in the extract was 99.7% and the yield was 95.3%.

The overall regulation of the recycling flow rate and the extract and raffinate flow rates in accordance with the invention resulted in an overall gain of 0.7% in purity and 0.3% in yield.

We claim:

1. A process for regulating at least one flow rate of at least one fluid or effluent circulating in a simulated moving bed chromatographic adsorption unit containing an adsorbent and comprising at least three chromatographic zones, each of these zones being constituted by at least one column or column section, at least one point between two zones for injection of a feed to be fractionated, at least one point between two zones for injection of eluent, at least one extract extraction point between each eluent injection point and the feed injection point located downstream in the direction of circulation of the eluent and at least one raffinate extraction point between each point for injecting the mixture and the eluent injection point located downstream in the direction of circulation of the eluent, the ensemble of the columns or sections forming at least one closed loop containing at least one device for introducing an anisotropy of properties, the injection and extraction points of at least one column or section being shifted over time in the same direction, the process wherein each time that an injection point or an extraction point passes from one part to another of said device, a control device which controls a means for regulating the flow rate under consideration, which regulation is about a set value, is caused to stop temporarily, and substantially simultaneously said regulating means is caused to place itself in a position allowing it to approach the desired flow rate and to start to regulate said flow rate at the desired set value.

2. A process according to claim 1, in which said device introducing an anisotropy of properties is at least one recycling pump between the first and last column which introduces a pressure anisotropy.

3. A process according to claim 2, in which the first and last columns are connected by at least one recycling pump, and a pressure drop $\Delta P$ is established between the two columns and in which each time one of the extraction points passes from upstream to downstream of the pump or from downstream to upstream of the pump, the control device controlling the regulating means for the effluent flow rate which is regulated about a set value is caused to stop regulating temporarily and said regulating means is caused to place itself in the position allowing said regulating means to approach said flow rate for the new pressure $P+\Delta P$ and to start to regulate said flow rate about the set value.

4. A process according to claim 1, in which said anisotropy of properties is due to an initial imperfection of a device of the simulated moving bed chromatographic adsorption unit, or an imperfection in its operation which occurs during production at one point in the loop.

5. A process according to claim 1, in which two different flow rates are used during passage of a fluid or effluent from one zone to the next zone, each of said flow rates being regulated about a set value (a) and (b) and in which passage from a first flow rate (a) to a second flow rate (b) which is different to flow rate (a) is caused by causing the control device controlling the regulating means which is regulating about set value (a) to stop regulating temporarily and to cause the regulating means to place itself in the position allowing it to approach flow rate (b) and start to regulate flow rate (b) about the set value corresponding to flow rate (b).

6. A process according to claim 1, in which the flow rate regulating means is a variable opening valve, a variable speed pump which can operate by varying the frequency or voltage, a variable piston stroke pump or a means which can vary the flow rate by varying the pressure.

7. A process according to claim 1, in which the simulated moving bed is in counter-current mode.

8. A process according to claim 1, in which the simulated moving bed is in co-current mode.

9. A process according to claim 1, in which the feed comprises a mixture of aromatic hydrocarbons containing eight carbon atoms.

10. A process according to claim 1, in which the feed comprises a mixture of aromatic hydrocarbons containing ten carbon atoms.

11. A process according to claim 1, in which fluid or effluent flow is commenced downstream of the anisotropy before stopping the upstream flow, in the case of simulated counter-current, and in the case of simulated co-current, a flow is commenced upstream of the anisotropy before stopping the downstream flow.

12. A process according to claim 1, wherein the desired flow rate is achieved.

13. A process according to claim 2, in which said anisotropy of properties is due to an initial imperfection of a device of the simulated moving bed chromatographic adsorption unit, or an imperfection in its operation which occurs during production at one point in the loop.

14. A process according to claim 2, in which two different flow rates are used during passage of a fluid or effluent from one zone to the next zone, each of said flow rates being regulated about a set value (a) and (b) and in which passage from a first flow rate (a) to a second flow rate (b) which is different to flow rate (a) is caused by causing the control device controlling the regulating means which is regulating about set value (a) to stop regulating temporarily and to cause the regulating means to place itself in the position allowing it to approach flow rate (b) and start to regulate flow rate (b) about the set value corresponding to flow rate (b).

15. A process according to claim 4, in which two different flow rates are used during passage of a fluid or effluent from one zone to the next zone, each of said flow rates being regulated about a set value (a) and (b) and in which passage from a first flow rate (a) to a second flow rate (b) which is different to flow rate (a) is caused by causing the control device controlling the regulating means which is regulating about set value (a) to stop regulating temporarily and to cause the regulating means to place itself in the position allowing it to approach flow rate (b) and start to regulate flow rate (b) about the set value corresponding to flow rate (b).

16. A process according to claim 13, in which two different flow rates are used during passage of a fluid or effluent from one zone to the next zone, each of said flow rates being regulated about a set value (a) and (b) and in which passage from a first flow rate (a) to a second flow rate (b) which is different to flow rate (a) is caused by causing the control device controlling the regulating means which is regulating about set value (a) to stop regulating temporarily and to cause the regulating means to place itself in the position allowing it to approach flow rate (b) and start to regulate flow rate (b) about the set value corresponding to flow rate (b).

* * * * *